United States Patent
Gruszczynski, II et al.

[11] Patent Number: 5,872,317
[45] Date of Patent: Feb. 16, 1999

[54] METHOD FOR MEASURING WALL SHEAR STRESS DUE TO FLUID FLOW IN PIPING SYSTEMS

[75] Inventors: David W. Gruszczynski, II; Mark S. Fornalik; Svetlana Reznik, all of Rochester, N.Y.

[73] Assignee: Eastman Kodak Company, Rochester, N.Y.

[21] Appl. No.: 976,434

[22] Filed: Nov. 21, 1997

[51] Int. Cl.[6] .......................... G01N 11/10; G01N 11/00; G01N 3/24; G01F 1/28

[52] U.S. Cl. ........................ 73/841; 73/54.01; 73/861.71; 73/54.39

[58] Field of Search ............................... 73/53.01, 61.62, 73/54.01, 54.39, 861.08, 861.71, 841

[56] References Cited

U.S. PATENT DOCUMENTS

| | | | |
|---|---|---|---|
| 3,786,346 | 1/1974 | Lorenzi | 324/38 |
| 3,862,047 | 1/1975 | Weltman et al. | 252/62.52 |
| 4,464,928 | 8/1984 | Dealy | 73/54 |
| 4,790,187 | 12/1988 | Tsinober et al. | 73/432.1 |
| 4,854,174 | 8/1989 | Keith | 73/714 |
| 4,859,943 | 8/1989 | Evans et al. | 324/216 |
| 4,879,899 | 11/1989 | Leehey | 73/147 |
| 5,047,717 | 9/1991 | Hofer | 324/209 |
| 5,052,228 | 10/1991 | Haritonidis | 73/705 |
| 5,142,227 | 8/1992 | Fish | 324/209 |
| 5,164,669 | 11/1992 | Namkung et al. | 324/209 |
| 5,166,613 | 11/1992 | Perry | 324/209 |
| 5,199,298 | 4/1993 | Ng et al. | 73/54.01 |

OTHER PUBLICATIONS

David Timperley, "The Effect of Reynolds Number and Mean Velocity of Flow n the Cleaning In–Place of Pipelines", Apr. 1981, 402–412.

*Primary Examiner*—Hezron Williams
*Assistant Examiner*—Jay L. Politzer
*Attorney, Agent, or Firm*—Mark G. Bocchetti

[57] ABSTRACT

A method and apparatus for measuring wall shear stress in pipe as a result of fluid flow therethrough employs a glass flow tube, magnetic particles of sufficiently small size such that the form drag force on the individual particles is orders of magnitude smaller than the viscous shear forces on the particle, and a magnet of known magnetic field strength. The glass flow tube with a known coefficient of friction allows visual inspection of particle release and further allows for the determination of the frictional forces on the particles. The magnetic particles are placed inside the tube with the magnet held in close proximity to the exterior wall of the tube. With the particles in place, fluid flow is initiated. The magnetic field strength at the surface of the flow tube is then reduced until the magnetic particles are hydrodynamically dislodged from the interior of the glass tube. Magnetic field strength may be reduced either by retracting the magnet away from the glass tube or by using an electromagnet and reducing current thereto. The position of the magnet, or the current to the electromagnet, at which the particles are dislodged is used to qualitatively determine the wall shear stress.

16 Claims, 7 Drawing Sheets

METHOD FOR MEASURING WALL SHEAR STRESS DUE TO FLUID FLOW IN PIPING SYSTEMS

FIELD OF THE INVENTION

This invention relates generally to the measurement of wall shear stress on the interior wall of pipe generated by the flow of fluid therethrough and, more particularly, to a method of measurement of wall shear stress utilizing magnetic particles in the fluid stream and a magnet of known magnetic field strength outside of the pipe to determine hydrodynamic cleaning effect of a fluid flow through the pipe.

BACKGROUND OF THE INVENTION

A variety of measurement techniques have been employed to measure the wall shear stress generated by fluid flow through pipe. One such method is the pressure gradient technique which relies on the measurement of pressure drop resulting from the flow of a fluid of known rheological properties through a piece of process equipment with known geometry and surface finish. The wall shear stress within the process equipment is related to the process geometry and solution properties through the Navier-Stokes equation. This method is typically used for tubular geometries where the governing relationships are well understood.

Other indirect methods of measurement of wall shear stress include the Preston Tube and Stanton Tube techniques. These techniques utilize specially designed probes with tiny openings facing into the flow, adjacent to the wall. The impact pressure measured in these probes is characteristic of the velocity profile adjacent to the wall and, therefore, also of the shear stress.

Another indirect method for measuring wall shear stress is the Hot Film Anemometer technique which measures fluid shear stress by measuring the changes in heat transfer from a small, electrically heated sensor exposed to the fluid motion. Heat transfer from the probe is governed by the thermal boundary layer which depends on the solution properties and velocity profile in the tube.

Still another method of indirectly measuring wall shear stress is the Diffusion Controlled Electrolysis technique. This technique measures the local wall shear stress from a mass transfer coefficient measured on a small surface element. The mass transfer is determined electrolytically. The small surface element forms one electrode and a much larger (non-controlling) electrode is placed elsewhere in the system. As the voltage between the electrodes is increased, the ion concentration at the cathode surface falls to zero. The current is then governed by the diffusion of the ions through the boundary layer adjacent to the cathode. The mass transfer is then correlated to the wall shear stress.

There is a method of direct measurement of wall shear stress known as the Floating Element technique. This technique utilizes a "floating" tubular section which is exposed to the fluid flow at the interior surface thereof with the floating tubular section being attached to an outer shell with strain measurement devices. The floating section is moved by the wall shear stress exerted by the fluid and the deflection of the floating element is measured. Multiple techniques have been identified for the measurement of the floating element deflection, including piezoelectric crystals and proximity sensitive detectors.

Another method of direct measurement of wall shear stress is the Micromachined Floating Element technique. This technique uses the same measurement concept as that of the Floating Element technique. However, the "floating" section being moved by the fluid flow in the micromachined floating element technique is small as compared to that of the floating element technique.

U.S. Pat. No. 4,464,928 to Dealy discloses an apparatus for measuring wall shear stress where the force that a fluid exerts on a plate, the surface of which is coplanar with the wall of the apparatus, is measured. Several techniques are discussed as possible methods for measuring of the deflection of the plate and, therefore, the force on the plate, including piezoelectric crystals and proximity sensitive detectors. This method is similar to the Micromachined Floating Element technique discussed above.

U.S. Pat. No. 4,790,187 to Tsinober et al discloses a method for measuring wall shear stress where several electrodes are extended into the fluid flow. A magnetic field is established between the electrodes and the shear stress is determined by measuring the relative movement of the electrodes which result in changes in the magnetic field.

U.S. Pat. No. 5,199,298 to Ng et al discloses a method for measuring wall shear stress where a sensor employs a silicon plate suspended about 1.4 microns above the surface of a silicon substrate by means of piezoresistive arms. Deflection of the piezoresistive arms results in a signal which can be converted into a shear stress measurement.

U.S. Pat. No. 4,854,174 to Keith discloses a method for measuring wall shear stress where a hot film shear stress gauge and a piezoelectric pressure transducer are coaxially located along the longitudinal centerline of a cylindrical metal shell. The hot shear stress gauge is exposed to the moving fluid while the pressure transducer is positioned directly below. The conductors attached to the hot film element provide power thereto while the conductors attached to the piezoelectric transducer transmit pressure produced electrical signals therefrom. This method is similar to the Hot Film Anemometer technique discussed above.

U.S. Pat. No. 4,879,899 to Leehey teaches a method for measuring walls shear stress where an elongate body having a longitudinal axis oriented transverse to fluid flow is disposed within the viscous sublayer of the turbulent boundary layer flow across a wall. The body has a plane of symmetry passing through the longitudinal axis of the body and normal to the wall. Torsional springs support the body for deflections about the longitudinal axis and deflections are measured. The angular deflections about the longitudinal axis are substantially linearly related to shear stress on the wall U.S. Pat. No. 5,052,228 to Haritonidis teaches a method which utilizes a micromachined diaphragm positioned across a gap from an end of an optic fiber. The optic fiber and the diaphragm are integrally mounted. The end of the optic fiber provides a local reference plane which splits light carried through the fiber toward the diaphragm. The light is split into a transmitted part which is subsequently reflected from the diaphragm, and a locally reflected part which interferes with the subsequently diaphragm reflected part. The interference pattern provides an indication of the magnitude and direction of diaphragm deflection. A second fiber optic provides an interference pattern that is out of phase with the first fiber. An interferometer sensor is used as a shear stress measuring device.

In an article entitled "The Effect of Reynolds Number and Mean Velocity of a Flow on Cleaning-In in Place of Pipelines" by D. Timperley, Timperley examined the relationship between microorganism removal and two cleaning solution flow parameters. Those parameters are Reynolds number and mean flow velocity. Timperley examined several flow rates for two different pipe diameters and concluded that microorganism removal correlated with mean flow velocity of the cleaning flow. Timperley then performed a theoretical analysis examining the correlation between the three parameters known to influence the cleaning action of turbulent flow, those being wall shear stress, thickness of the laminar boundary layer, and velocity at the edge of the laminar sublayer, and the measured cleaning solution flow parameters (Reynolds number and mean flow velocity). Timperley's theoretical evaluation showed that the shear stress, as calculated by a turbulent wall shear stress model, the thickness of the laminar boundary layer, and the velocity at the edge of the laminar sublayer all correlated to the mean flow velocity of the cleaning solution and not to the Reynolds number of the cleaning solution.

The prior art fails to teach a method for measuring wall shear stress within a pipe which uses particles adhered to the interior wall of the pipe by a known force such that shear stress can be determined through observation of the removal of such particles with hydrodynamic flow.

SUMMARY OF THE INVENTION

It is, therefore, an object of the present invention to provide a method for measuring the wall shear stress generated by fluid flowing through a pipe using particulates held against and potentially adhered to the interior wall of the pipe.

It is a further object of the present invention to provide a method for measuring the wall shear stress generated by a fluid flowing from a pipe using magnetic particles in a glass tube, the particles being held in place with a magnet proximately located to the glass tube.

Yet another object of the present invention is to provide a method for measuring the wall shear stress for fluid flowing through a pipe which enables the evaluation of hydrodynamic cleaning effect independent of other cleaning effects such as solubility of the fouling to be removed.

Briefly stated, the foregoing and numerous other features, objects and advantages of the present invention will become readily apparent upon a reading of the detailed description, claims and drawings set forth herein. These features, objects and advantages are accomplished with an apparatus which employs a glass flow tube, magnetic particles of sufficiently small size such that the form drag force on the individual particles is orders of magnitude smaller than the viscous shear forces on the particle, and a magnet of known magnetic field strength. The flow tube must be a transparent material with a known coefficient of friction thereby allowing visual inspection of particle release and further allowing for the determination of the frictional forces on the particles. Glass is, therefore, the preferred material for the flow tube. The magnetic particles are placed inside the tube with the magnet held in close proximity to the exterior wall of the tube. With the particles in place, fluid flow is initiated. The magnet is then moved away from the glass tube thereby reducing magnetic field strength at the tube until the magnetic particles are hydrodynamically dislodged from the interior of the glass tube. The position of the magnet at which the particles are dislodged is used to qualitatively determine the wall shear stress. Alternatively, the magnet position is correlated to wall shear stress through a first order force balance using the equation below:

$$F_H = \mu(F_N - L) \tag{1}$$

Where: $F_H$ is the hydrodynamic cleaning force;

$\mu$ is the coefficient of friction;

$F_N$ is the sum of the magnetic and the attractive forces normal to the pipe wall; and L is the lift force.

Lift force (L) is a function of the size and shape of the particle. Methods for calculation of lift force (L) are available and known to those skilled in the art as evidenced by "Handbook of Multiphase Systems" by Gad Hetsroni.

As mentioned above, the measurement system of the present invention can be used either qualitatively or quantitatively. The measurement can be used for comparison of flow conditions for determination of hydrodynamic cleaning effect on a relative scale (based upon the magnetic force) or, if desired, the actual removal hydrodynamic cleaning force can be calculated either through the first order approximation of Equation (1) stated above or by more complex models of the system. Through the variation of single phase and two phase flow parameters, wall shear stress (and, therefore, hydrodynamic cleaning effects) can be determined for a variety of flow conditions within a piping system.

DETAILED DESCRIPTION OF THE INVENTION

Figure 1:
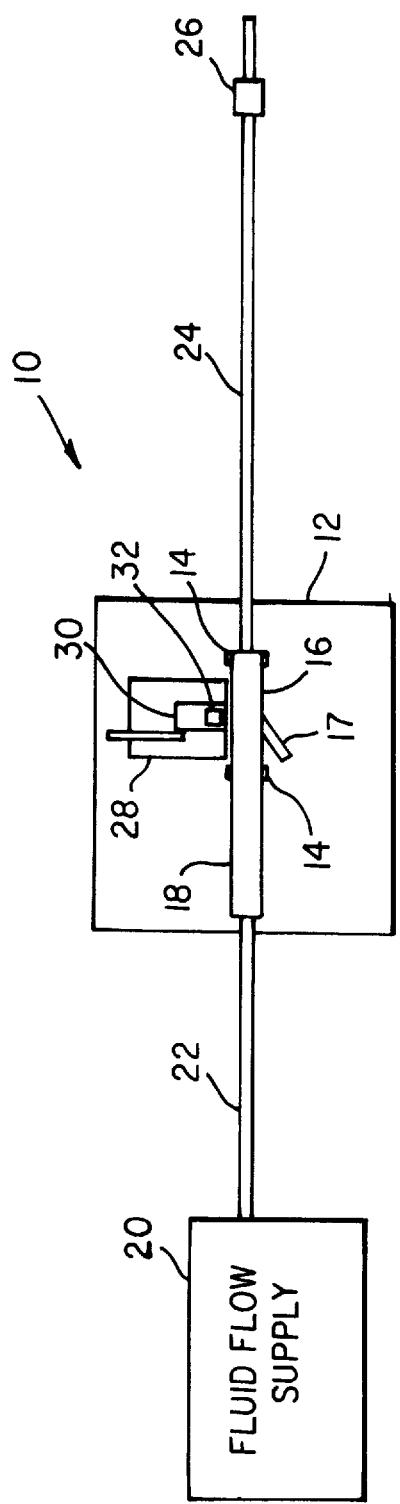
FIG. 1 is a schematic top plan view of the magnetic particle wall shear stress measurement apparatus of the present invention.
Figure 2:
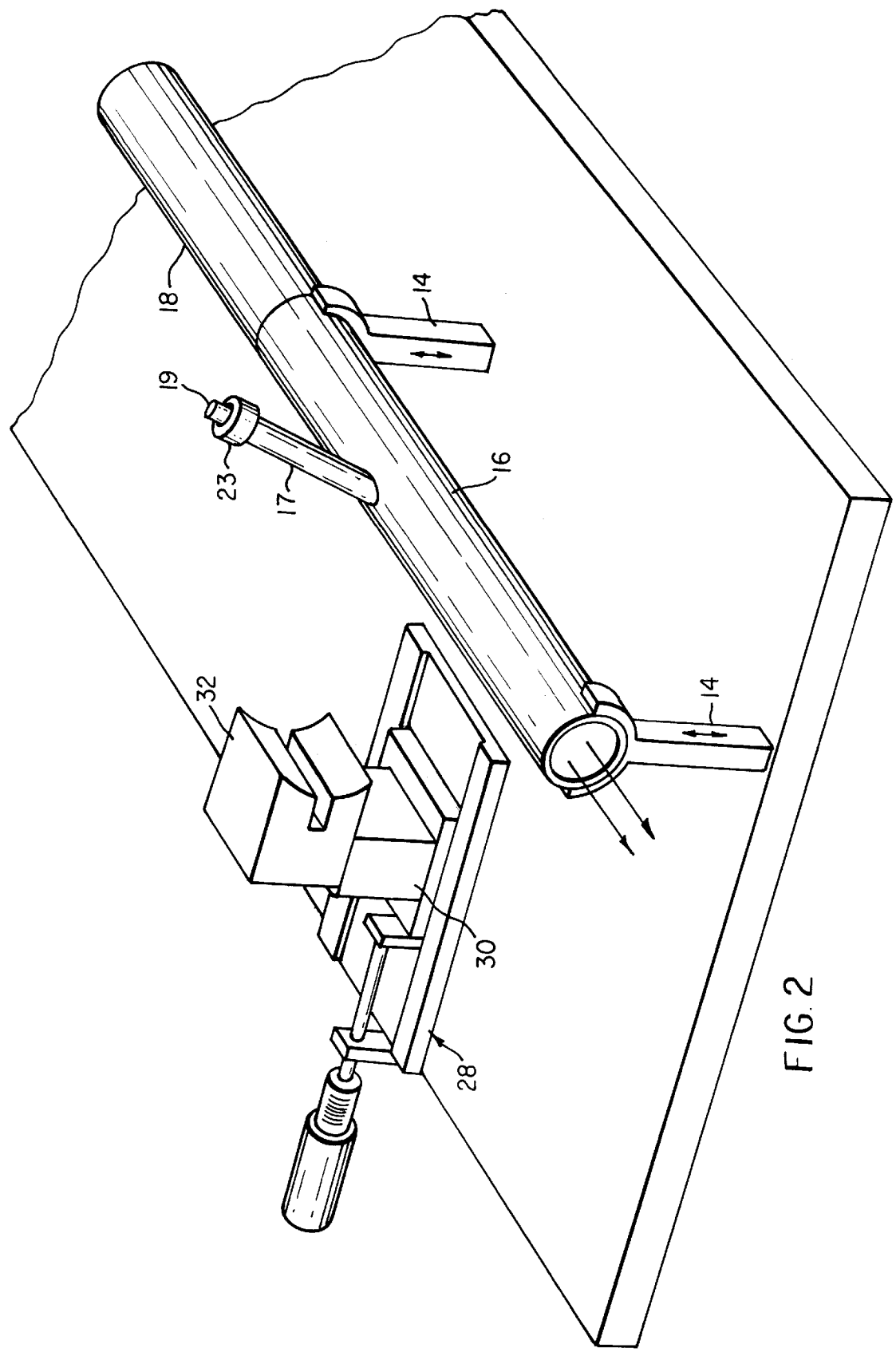
FIG. 2 is a perspective view of the magnetic particle wall shear stress measurement apparatus of the present invention.

Turning first to FIG. 1, there is schematically depicted a top plan view of the magnetic particle wall shear stress measurement apparatus 10 of the present invention. The apparatus 10 includes a base plate 12 having a pair of adjustable supports 14 mounted thereon (shown more clearly in FIG. 2). Base plate 12 and adjustable supports should be made of a non-magnetic material. Adjustable supports 14 support a glass flow tube 16. Glass tube 16 preferably includes an access port 17 allowing for easier access to insert magnetic particles into glass tube 16. Access port 17 can be angled or perpendicular to the cylindrical axis of flow tube 16. If access port 17 is angled, it should positioned such that the entrance thereto is directed upstream. A plug 19 inserts into access port 17 (see FIG. 10). Plug 19 should almost completely fill access port 16 such that the distal end 21 of plug 19 is approximately flush with the interior wall of glass tube 16. A cap 23 and an O-ring 25 may be used to respectively retain and seal plug 16 in access port 17. There is a transparent or clear tube 18 (preferably made of Lexan®) connected to glass tube 16. The inside diameter of transparent tube 18 should be the same as the inside diameter of glass flow tube 16. There is a fluid supply 20 connected by means of inlet conduit 22 to tube 18. Fluid supply 20 can supply a liquid such as, for example, water for single phase flow or, alternatively, can supply both a liquid and a gas (such as air) to generate a two phase flow into inlet conduit 22. If fluid supply 20 has any magnetic components, it should located a sufficient distance from magnet assembly 32 and glass tube 16 to ensure that it does not significantly influence the magnetic field of magnet assembly 32. There is an outlet conduit 24 connected to discharge side of glass tube 16. Inlet conduit 22 and outlet conduit 24 should have the same inside diameter as flow tube 16 in order to minimize their influence on the flow conditions within flow tube 16. A valve 26 in outlet conduit 24 allows for the back pressure of the apparatus 10 to be adjusted to a desired or predetermined level.

Attached to base plate 12 is a linear slide mechanism 28. Mounted to linear slide mechanism 28 is a magnet support bracket 30 supporting magnet assembly 32 thereon. Linear slide mechanism 28 allows for magnet assembly 32 to be controllably moved toward and away from glass tube 16. Linear slide mechanism 28 and magnet support bracket 30 should be made of a non-magnetic material. Adjustable supports 14 allow the height at which glass tube 16 resides to be adjusted such that the centerline thereof is at the same height above base plate 12 as is the centerline of magnet assembly 32.

Figure 3:
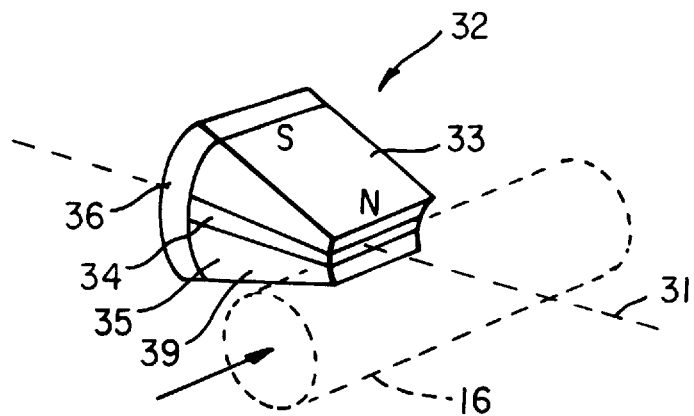
FIG. 3 is a perspective view of the preferred shape magnet for use with the apparatus of the present invention.
Figure 4:
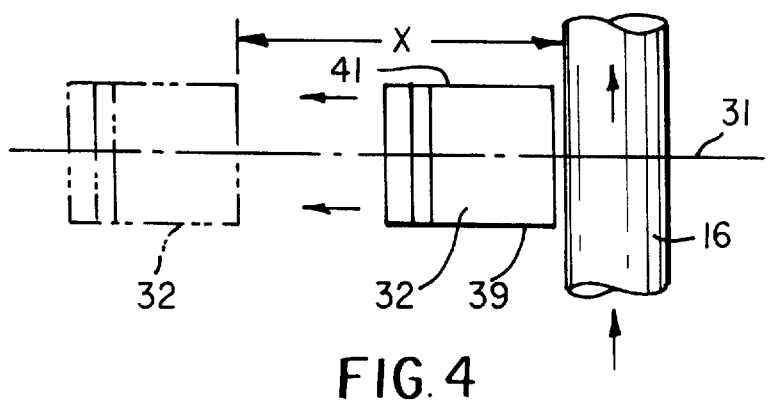
FIG. 4 is a top plan view of the magnet positioned adjacent the glass flow tube.

The magnet assembly 32 preferably generates a uniform magnetic field which is strongest along central axis 31. A magnetic field without discontinuities is essential for the quantification of particle removal. In other words, a uniform magnetic field is necessary such that stray forces which may influence particle removal are eliminated. One example of a shape for magnet assembly 32 which produced a focused symmetric magnetic field pattern is a wedge shape as depicted in FIGS. 3 and 4. Magnet assembly 32 actually consists of a pair of wedge-shaped magnets 33, 35 separated by a spacer 34, all mounted within a backer plate 36. Magnets 33, 35 are magnetically oriented opposite to one another. That is, if magnet 33 is oriented north (N) and south (S) as indicated in FIG. 3, magnet 35 would be oriented such that the south pole would be at that end of magnet 35 proximate to glass tube 16. Magnets 33, 35 are preferably made from a permanent magnetic material that has high remanent magnetization, high coercive force, high magnetic energy product, and is easy to process. Neodymium Iron Boron (NdFeB) is an example of such a material. Backer plate 36 is preferably made of a magnetically conductive material such as a ferromagnetic alloy. Spacer 34, which is preferably a flat plate of non-magnetic material which separates magnets 33, 35, assists in establishing a uniform, cylindrical magnetic field. Backer plate 36 is used to complete the circuit of the magnet assembly 32 to thereby focus the magnetic feld which otherwise be "leaking" out of the back of the magnets 33, 35. Backer plate 36 thus directs the energy to the front of magnet assembly 32 thereby strengthening the magnetic field. Thus, magnets 33, 35, in combination with backer plate 36, form what is, in essence, a horseshoe magnet. The front surface 37 of magnet assembly 32 is preferably concave or arcuate and has a radius of curvature which approximates the radius of flow tube 16. Magnet assembly 32 has an upstream face 39 and downstream face 41 with the width of magnet assembly 32 being the distance between upstream face 39 and downstream face 41.

The geometry of magnet assembly 32 can, of course, be changed to meet specific needs. If a greater or lesser magnetic field strength is required, the dimensions of magnets 33, 35, spacer 34 and backer plate 36 can be sized accordingly. By narrowing the width of magnet assembly 32 a more focused magnetic field can be achieved. A more focused magnetic field would be useful if it is desired to examine the movement of individual magnetic particles in glass tube 16.

Two different magnetic particles were evaluated for use with the present invention. Those particles were Strontium Ferrite particles as obtained from Powdertech Corp., of Valparaiso, Ind. and Ancor EH 80/150 particles as obtained from Hoeganaes, an Interlake Company, of Riverton, N.J. The Strontium Ferrite particles ranged in diameter from 2 to 40 microns with a mean diameter of approximately 8 microns. The Ancor EH80/150 particles ranged in diameter from 80 to 150 microns. Testing was initially planned with both particle types. However, it was found that the magnetic field strength of the magnet being used for testing was insufficient to hold the Strontium Ferrite particles in place. In other words, the particles were hydrodynamically removed at low flow conditions while magnet assembly 32 was positioned immediately adjacent glass tube 16. This was believed to be the result of the small mass and/or relatively weak magnetic properties of the Strontium Ferrite particles. Thus, the Ancor EH80/150 particles were used in testing the operation of apparatus 10. The smaller Strontium Ferrite particles could be used in the practice of the present invention provided that a magnet assembly 32 having sufficient magnetic field strength is used.

In order to use the apparatus 10 of the present invention, the fluid supply is turned on and the desired flow conditions are established through transparent tube 18 and glass tube 16. Those desired flow conditions may establish single phase or two phase flow as mentioned above. Further, the back pressure through the apparatus 10 is adjusted. In such manner, the flow conditions through clear tube 18 and glass tube 16 can mimic the flow conditions through a particular piping system which it is desired to hydrodynamically clean. With the desired or predetermined process flow conditions established, the fluid supply is turned off. The magnetic particles are then inserted into glass tube 16. Using linear slide mechanism 28, magnet assembly 32 is positioned adjacent to glass tube 16. Fluid flow at the predetermined flow conditions is then reestablished through Lexan® tube 18 and glass tube 16. Using linear slide mechanism 28, magnet assembly 32 is slowly retracted away from glass tube 16. Retracting magnet assembly 32 away from flow tube 16 serves to decrease the strength of the magnetic field at flow tube 16. The distance "x" (see FIG. 4) of magnet assembly 32 from flow tube 16 and the position of the magnetic particles with respect to the front surface 37 of the magnet assembly 32 are recorded when the particles release from the wall of glass tube 16 and exit into outlet conduit 24. Particle release is measured from the centerline of magnet assembly 32.

Operationally, there are several sources of variability in the measurement process. Those sources include variations in particle size, variations in particle quantity, speed of magnet retraction, the nature of the fluid flow, and operator interpretation of "particle release". The strength of the magnet assembly 32 was insufficient to hold individual particles in place. Therefore, a collection or clumped mass of particles was used. Variability in the mass of the particles used resulted in measurement variability. In order to minimize this, the particle mass was maintained between 0.005 and 0.012 grams. If particles clumped during the experiment resulting in a mass outside of the specified range, the results were discarded.

The speed at which magnet assembly 32 was retracted and the nature of fluid flow combined as a source of variability. The different fluid flow rates possessed different pulse frequencies for two-phase flow (from the fluid delivery system 20). Two-phase flow of a liquid and a gas may take various forms such as slug, annular, wavy, etc. For two-phase flow conditions where the pulse frequency was low, if the magnet was retracted too quickly, the measurement would indicate that removal of the particles occurred while the position of magnet assembly 32 was far from the wall of glass tube 16. This would result in an under estimate of the actual wall shear stress and, thus, the hydrodynamic cleaning effect of the fluid flow. Thus, there is a need to control the speed of retraction of magnet assembly 32 away from the wall of glass tube 16. The speed of retraction should be correlated to the pulse frequency. A slower rate of retraction should be used when the pulse frequency is low and a higher rate of retraction can be used when the pulse frequency is higher.

Another source of variability is the potential for misinterpreting what constitutes a "particle release". During operation of the apparatus 10 of the present invention, the particles may be momentarily dislodged from their original positions in glass tube 16 and then be trapped once again by the magnetic field further downstream (typically less than about 0.1 inches downstream). This particle sliding can occur frequently. Eventually, however, the particles are dislodged completely and are swept downstream out of glass tube 16. It is the removal of a particle completely from glass tube 16 which constitutes particle release. Particle release is determined by visual inspection. This can be done through direct observation by the operator of apparatus 10. Alternatively, visual inspection can be performed by recording the particle removal on some recording medium such as using a high speed camera and a zoom lens to photograph particle removal. Visual inspection can also be achieved by videotaping particle removal.

Figure 5:
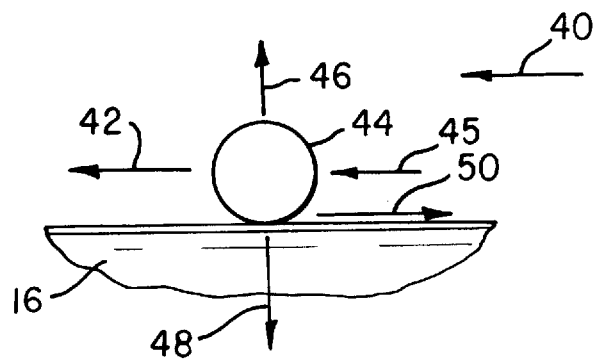
FIG. 5 is a force diagram of the forces exerted on an individual magnetic particle held against the wall of the glass tube in the magnetic field of the magnet.

FIG. 5 is a force diagram for the forces exerted on an individual particle held against the wall of glass tube 16 in the magnetic field of magnet assembly 32. Arrow 40 represents the direction of fluid flow through glass tube 16. Arrow 42 represents the viscous drag force, $F_H$, exerted on particle 44 as a result of the fluid flowing through glass tube 16. Arrow 45 represents the form drag force on the particle again as the result flow aorund the particle. Arrow 46 represents the lift force, L, exerted on the particle 44 as a result of fluid flowing through glass tube 16. Arrow 48 represents the normal forces, $F_N$, exerted on particle 44, those normal forces being the sum of the magnetic attractive force exerted by magnet assembly 32 and the adhesive forces generated between particle 44 and the interior wall of glass tube 16. Arrow 50 represents the frictional force, F, resulting from the friction between the interior wall of glass tube 16 and particle 44. The frictional force is calculated using the equation:

$$F = \mu(F_N - L) \quad (2)$$

Figures 6, 10:
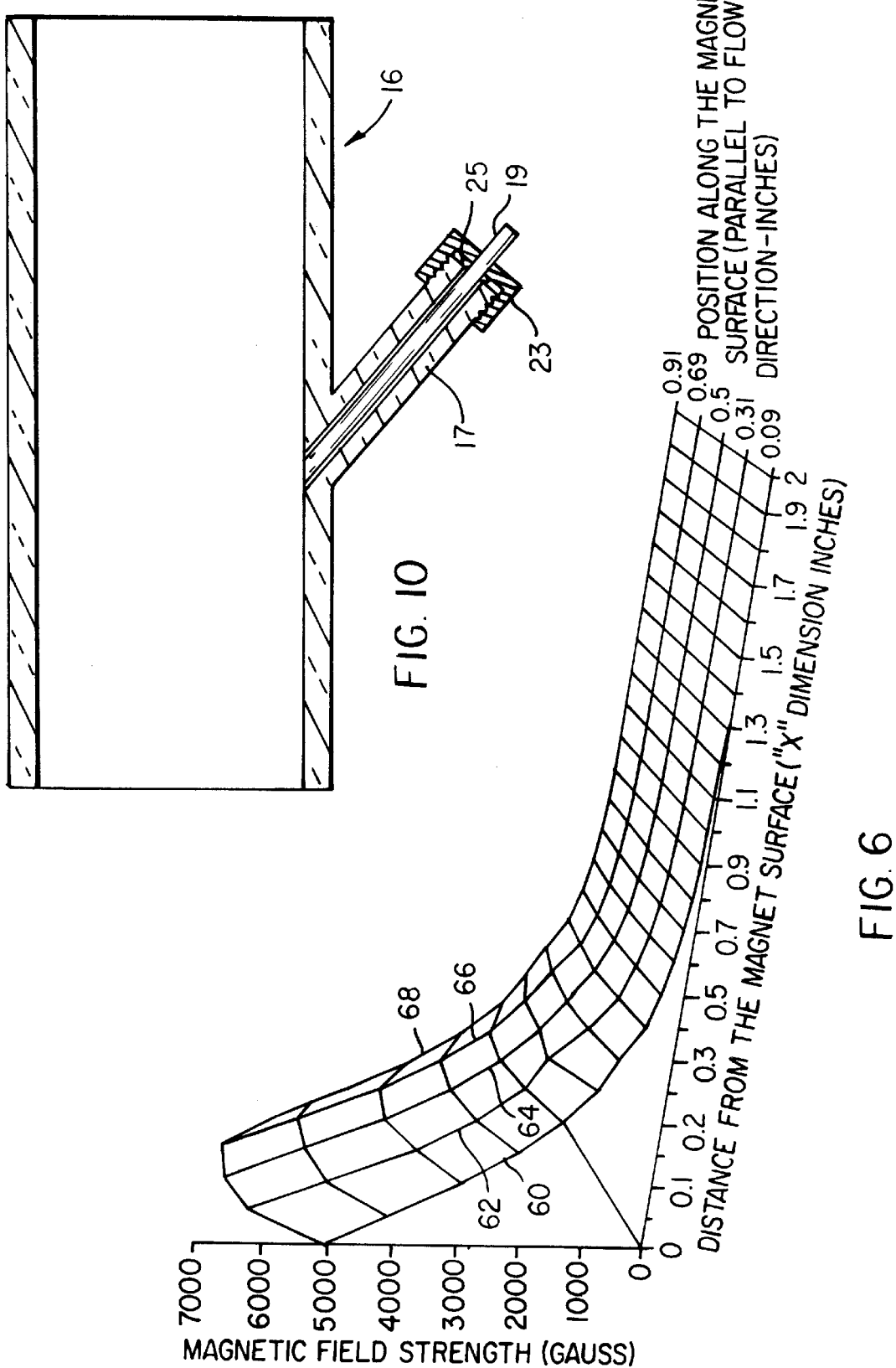
FIG. 6 is a graph plotting the measured magnetic field strength of the magnet versus distance from the magnet surface.
FIG. 10 is a cross-sectional view of the flow tube.

FIG. 6 depicts a graph plotting the measured magnetic field strength of magnet assembly 32 (shown in FIGS. 3 and 4) versus distance from the magnet surface. The magnet assembly 32 used for test purposes had a width of one inch. Each wedge-shaped magnet 33, 35 was one inch by one inch with a thickness of ⅜" at its thickest point. Spacer 34 was 1" by 1" by ⅛". FIG. 6 actually shows five curves plotting magnetic field strength at five separate locations along the width of magnet assembly 32. Thus, curve 60 plots magnetic field strength versus the distance from flow tube 16 to concave surface 37 at a location 0.09 inches from upstream surface 39 along concave surface 37. Curve 62 plots magnetic field strength versus the distance from flow tube 16 to concave surface 37 at a location 0.31 inches from upstream surface 39 along concave surface 37. Curve 64 plots magnetic field strength versus the distance from flow tube 16 to concave surface 37 at a location 0.5 inches from upstream surface 39 along concave surface 37. Curve 66 plots magnetic field strength versus the distance from flow tube 16 to concave surface 37 at a location 0.69 inches from upstream surface 39 along concave surface 37. Curve 68 plots magnetic field strength versus the distance from flow tube 16 to concave surface 37 at a location 0.91 inches from upstream surface 39 along concave surface 37.

Figure 7:
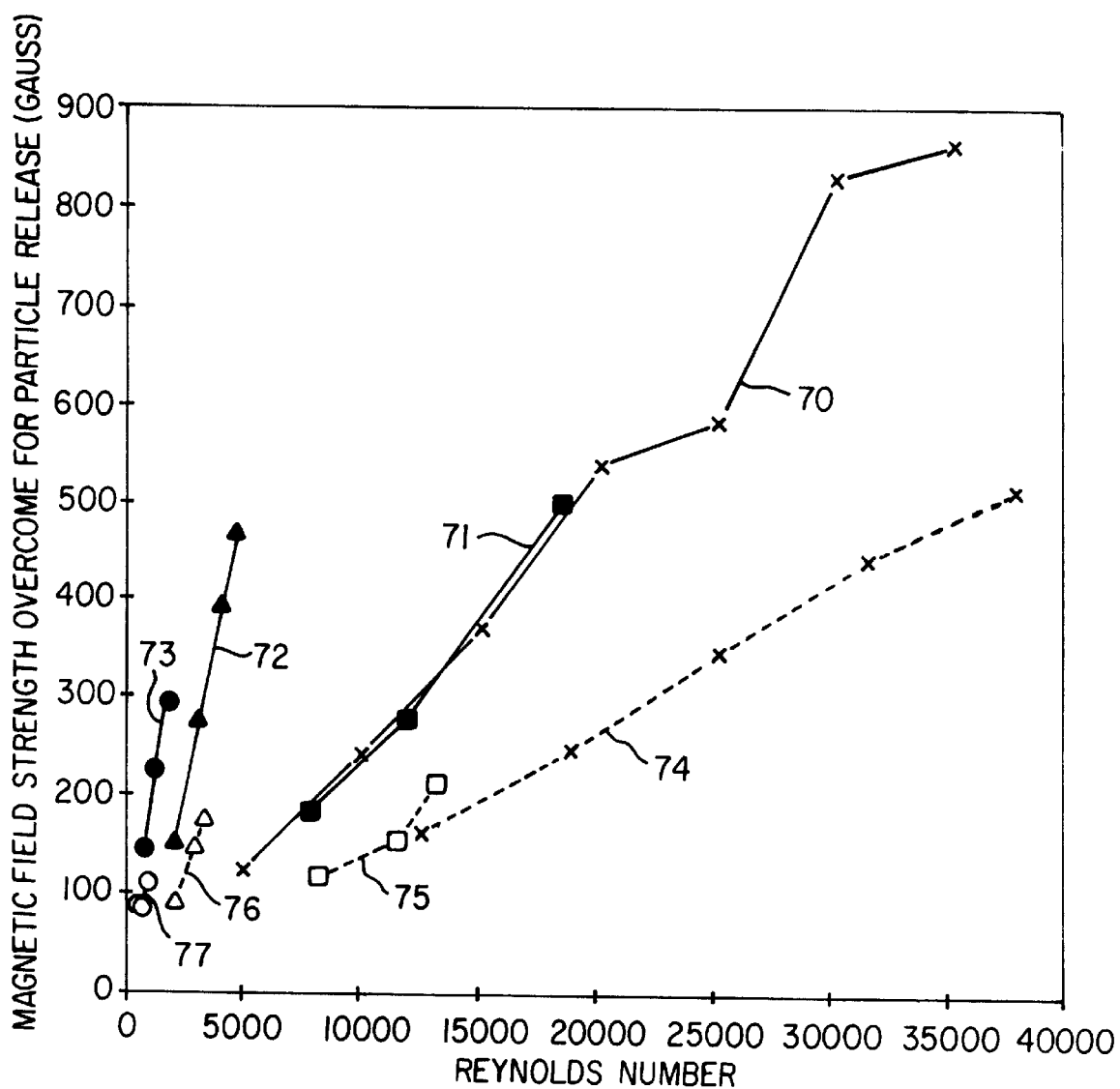
FIG. 7 is a graph plotting magnetic field strength overcome from particle release versus Reynolds number using the magnetic particle wall shear stress measurement technique of the present invention.
Figure 8:
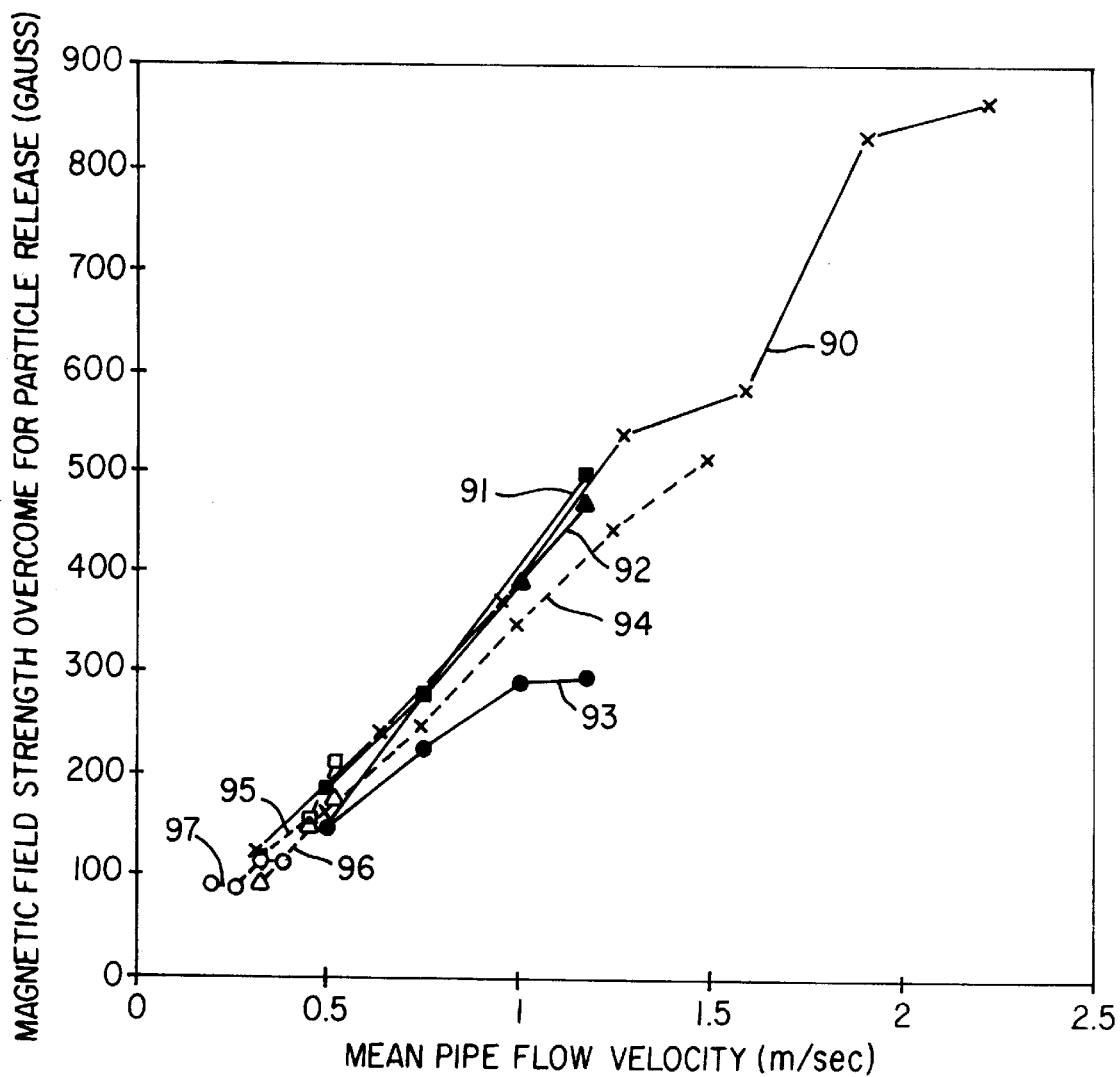
FIG. 8 is a graph plotting magnetic field strength overcome from particle release versus mean pipe flow velocity using the magnetic particle wall shear stress measurement technique of the present invention.
Figure 9:
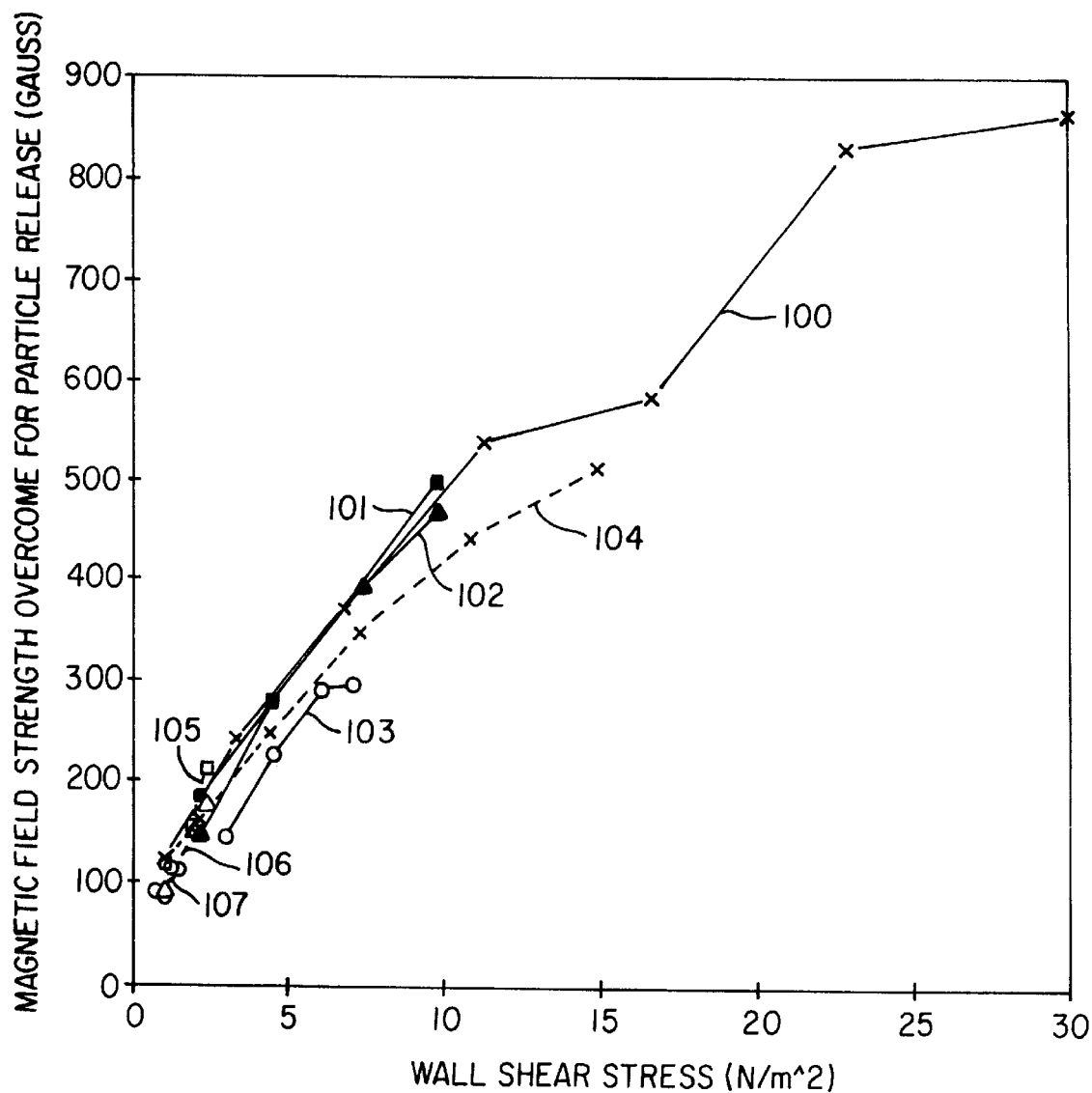
FIG. 9 is a graph plotting magnetic field strength overcome from particle release versus wall shear stress using the magnetic particle wall shear stress measurement technique of the present invention.

The magnetic particle wall shear stress measurement method of the present invention was used to duplicate the analysis performed by Timperley. An experiment was conducted which examined the effects of flow rates (at several levels), pipe diameter (two sizes), and solution viscosity (three different viscosities). The magnetic particle wall shear stress measurement method of the present invention was used to measure the relative force required to remove the particles from the glass tube 16 by the cleaning flow. The data from the test was correlated to the Reynolds number of the cleaning solution. This correlation is depicted in the graph of FIG. 7. The test data plotted in FIG. 7 shows several different groupings in the data. In particular, the data shows trends with both viscosity and pipe diameter which indicates there is no correlation with Reynolds number. This is consistent with Timperley's data and conclusions. Tests A and B which generated curves 70 and 71 were conducted using a flow tube 16 having an inside diameter of 0.62 inches and a fluid having a viscosity of 1 cP (water). Test C which generated curve 72 was conducted using a flow tube 16 having an inside diameter of 0.62 inches and a fluid having a viscosity of 4.4 cP (glycerin solution). Test D which generated curve 73 was conducted using a flow tube 16 having an inside diameter of 0.62 inches and a fluid having a viscosity of 12 cP (glycerin solution). Tests E and F which generated curves 74 and 75 were conducted using a flow tube 16 having an inside diameter of 1.0 inch and a fluid having a viscosity of 1 cP (water). Test G which generated curve 76 was conducted using a flow tube 16 having an inside diameter of 1.0 inch and a fluid having a viscosity of 4.4 cP (glycerin solution). Test H which generated curve 77 was conducted using a flow tube 16 having an inside diameter of 1.0 inch and a fluid having a viscosity of 12 cP (glycerin solution). The data from Tests A through H is also correlated to the mean flow velocity of the cleaning solution as depicted in the graph of FIG. 8. FIG. 8 shows that all of the data follows the same trend, regardless of diameter of glass tube 16 or solution viscosity (with the exception of the 12 cP, one inch ID glass tube data). Curves 90, 91, 92, 93, 94, 95, 96 and 97 were generated with the data from Tests A through H, respectively. The data from Tests A through H was further correlated to the calculated wall shear stress of the cleaning solution as depicted in the graph of FIG. 9. Curves 100, 101, 102, 103, 104, 105, 106 and 107 were generated with the data from Tests A through H, respectively. Because of the wide variety of cleaning viscosities, flow rates, and pipe diameters, both the laminar and turbulent wall shear stress models were used to generate the data. The laminar wall shear stress equation used was:

$$\tau_L = (4*V*\mu)/R$$

Where: $\tau_L$ is the laminar wall shear stress (N/m$^2$)
V is the average flow velocity (m/sec)
$\mu$ is the viscosity (kg/(sec*km)
R is the radius of the pipe (m).
The turbulent wall shear stress equation was:

$$\tau'_T = 0.03325 \rho V^2 \left(\frac{v}{RV}\right)^{0.25}$$

Where: $\tau_T$ is the turbulent wall shear stress (N/m$^2$)
V is the average flow velocity (m/sec)
v is the kinematic viscosity (m$^2$/sec)
$\rho$ is the density of the solution (kg/m$^3$)
R is the radius of the pipe (m).

FIG. 9 shows that the experimental data correlates with the wall shear stress. Thus, the data collected using the magnetic particle wall shear stress measurement method of the present invention confirmed the correlation between cleaning efficiency and mean flow velocity. In addition, the output of the magnetic particle wall shear stress measurement method was directly correlated to the wall shear stress for flows both in the laminar and turbulent flow regimes. This shows that the apparatus of the present invention is capable of measuring wall shear stress and establishing the correlation between wall shear stress and cleaning efficiency.

From the foregoing it can be seen that through a variation of process flow conditions through glass tube 16 and system back pressure, flow conditions through an actual piping system which is to be cleaned can be duplicated. Thus, through variation of such flow conditions, it can be determined which flow conditions generate the greatest wall shear stress and, thus, the greatest hydrodynamic cleaning efficiency for a particular piping system. With that established, the same flow conditions can be set up in the piping system to be cleaned.

It should be apparent to those skilled in the art that the size of the components of apparatus 10 are dependent on the data which the user wishes to gather. Thus, if the user wants wall shear stress measurement data for one inch diameter piping, then glass flow tube 16 should be sized to have the same nominal inside diameter as one inch piping. Similarly, if the user wants wall shear stress measurement data for 5/8" diameter tubing, then glass flow tube 16 should be sized to have the same nominal inside diameter as 5/8" diameter tubing. In either case, the length of flow tube 16 should be at least six inches. The transparent tube 18, as mentioned above, should have the same inside diameter as glass tube 16. The length of transparent tube 18 should be at least approximately 150 times the inside diameter in order to fully establish the desired flow conditions in glass tube 16.

It should be understood that flow tube 16 and transparent tube 18 can be integrally made. That is, a single transparent tube of appropriate length can be substituted for flow tube 16 and transparent tube 18. Using the combination of glass flow tube 16 and transparent tube 18 allows for ease of manufacture of the apparatus of the present invention as well as for a lower chance of damaging the flow tube 16 during set up of the apparatus or when placing magnetic particles 44 into glass flow tube 16. If a single transparent tube is used, it is preferable to make the tube from glass as opposed to a clear thermoplastic. Glass has a greater hardness and is therefore less subject to wear from erosion. Movement of the magnetic particles across the inside surface of a thermoplastic tube may result wear of such surface. Wear of the inside surface will result in a change in the coefficient of friction.

It should also be understood that the present invention can be practiced with a tube 18 which is not transparent. It is, however, preferred that tube 18 be made of a transparent material so that the operator can visually confirm that the desired flow conditions have been fully established prior flow tube 16.

In an alternative embodiment of the apparatus of the present invention, an electromagnet could be substituted for magnet assembly 32. An electromagnet could be mounted on a linear slide mechanism such that the apparatus 10 is operated identically to the preferred embodiment shown in FIGS. 1 and 2. Alternatively, rather than moving the electromagnet to decrease magnetic field strength at the flow tube 16, magnetic field strength at the flow tube 16 could be decreased by decreasing electric current to the electromagnet. The current to the electromagnetic would be measured at the point of particle release. There would be no need for a linear slide mechanism with this alternative embodiment incorporating an electromagnet.

From the foregoing, it will be seen that this invention is one well adapted to attain all of the ends and objects hereinabove set forth together with other advantages which are apparent and which are inherent to the apparatus and method.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in a limiting sense.

What is claimed is:

1. A method for measuring wall shear stress in pipe as a result of fluid flow therethrough, the method comprising the steps of:
   (a) establishing predetermined fluid flow conditions through a transparent flow tube having a known coefficient of friction;
   (b) stopping fluid flow to the transparent flow tube;
   (c) inserting a predetermined amount of magnetic particles into the transparent flow tube;
   (d) placing a magnet having a known magnetic field strength proximate to an exterior surface of the transparent flow tube;
   (e) reestablishing the predetermined fluid flow conditions through the transparent flow tube;
   (f) retracting the magnet away from the exterior surface of the transparent flow tube to a point where all of the predetermined amount of magnetic particles have been removed from the transparent flow tube; and
   (g) measuring a distance from the exterior surface of the transparent flow tube to the point; and
   (h) using the distance to determine wall shear stress.

2. A method as recited in claim 1 wherein:
   the predetermined flow conditions have a pulse frequency and said retracting step is performed at a speed which is regulated with the pulse frequency.

3. A method as recited in claim 1 wherein:

the predetermined flow conditions have a pulse frequency and said retracting step is performed at a speed which is directly proportional with the pulse frequency.

4. A method for measuring wall shear stress in pipe as a result of fluid flow therethrough, the method comprising the steps of:

(a) establishing predetermined fluid flow conditions through a transparent flow tube;

(b) stopping fluid flow to the transparent flow tube;

(c) inserting a predetermined amount of micro-sized magnetic particles into the transparent flow tube;

(d) placing a magnet having a known magnetic field strength proximate to an exterior surface of the transparent flow tube to hold the predetermined amount of micro-sized magnetic particles against an interior surface of the transparent flow tube;

(e) reestablishing the predetermined fluid flow conditions through the transparent flow tube; and (f) reducing magnetic field strength at the transparent flow tube such that all of the predetermined amount of magnetic particles have been released from the transparent flow tube; and (g) using magnetic field strength at the transparent flow tube to determine wall shear stress.

5. A method as recited in claim 4 wherein:

said reducing step is performed by retracting the magnet away from the transparent flow tube.

6. A method as recited in claim 4 wherein:

said magnet is an electromagnet and said reducing step is performed by reducing electric current to the electromagnet.

7. An apparatus for measuring wall shear stress in pipe resulting from fluid flow therethrough comprising:

(a) a transparent flow tube having a known inside diameter, said transparent flow tube having an interior surface having a known coefficient of friction;

(b) a magnet having a magnetic field of known strength;

(c) means for supporting said magnet adjacent an exterior surface of said transparent flow tube;

(d) means for retracting said magnet away from the exterior surface of said transparent flow tube;

(e) a plurality of magnetic particles residing within said transparent flow tube; and (f) means for establishing predetermined fluid flow conditions through said transparent flow tube; and (g) means for relating a distance of retraction of said magnet to wall shear stress.

8. An apparatus as recited in claim 7 wherein:

said transparent flow tube is a glass tube.

9. An apparatus as recited in claim 7 further comprising:

an inlet tube connected colinearly with said transparent flow tube, said inlet tube having an inside diameter which is the same as the known inside diameter of said transparent flow tube.

10. An apparatus as recited in claim 7 wherein:

said magnetic particles are sized such that a form drag force on an individual magnetic particle resulting from fluid flow through said transparent flow tube is orders of magnitude smaller than viscous shear forces on the individual magnetic particle.

11. An apparatus as recited in claim 7 wherein:

said magnet is shaped such that said magnetic field is uniform and strongest along a central axis of said magnet.

12. An apparatus as recited in claim 7 wherein:

said magnet is wedge shaped.

13. An apparatus for measuring wall shear stress in pipe resulting from fluid flow therethrough comprising:

(a) a transparent flow tube having a known inside diameter, said transparent flow tube having an interior surface having a known coefficient of friction;

(b) a magnet having a magnetic field of known strength;

(c) means for supporting said magnet adjacent an exterior surface of said transparent flow tube;

(d) means for controlling the magnetic field strength at said transparent flow tube;

(e) a plurality of magnetic particles residing within said transparent flow tube; and (f) means for establishing predetermined fluid flow conditions through said transparent flow tube; and (g) means for relating the magnetic field strength to wall shear stress.

14. An apparatus as recited in claim 13 wherein:

said magnet is an electromagnet and said means for controlling is through varying electric current to said electromagnet.

15. An apparatus as recited in claim 13 wherein:

said means for controlling is a means for retracting said magnet away from the exterior surface of said transparent flow tube.

16. An apparatus as recited in claim 13 wherein:

said magnet is a permanent magnet and said means for controlling is a means for retracting said magnet away from the exterior surface of said transparent flow tube.

* * * * *